United States Patent
Zisterer et al.

(10) Patent No.: US 6,572,632 B2
(45) Date of Patent: Jun. 3, 2003

(54) INSTRUMENT FOR CUTTING BIOLOGICAL AND NOTABLY HUMAN TISSUE

(75) Inventors: Uwe Zisterer, Koblingen (DE); Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/945,602

(22) Filed: Sep. 4, 2001

(65) Prior Publication Data

US 2002/0035372 A1 Mar. 21, 2002

Related U.S. Application Data

(62) Division of application No. PCT/EP00/01547, filed on Feb. 25, 2000.

(51) Int. Cl.$^7$ .............................................. A61B 17/32
(52) U.S. Cl. ....................................... 606/170; 606/180
(58) Field of Search ................................ 606/184, 180, 606/170; 604/22; 600/566, 567

(56) References Cited

U.S. PATENT DOCUMENTS

| | | | |
|---|---|---|---|
| 4,174,715 A | 11/1979 | Hasson | 128/321 |
| 5,520,634 A | 5/1996 | Fox et al. | 604/22 |
| 5,674,237 A | 10/1997 | Ott | 606/185 |
| 5,697,947 A | 12/1997 | Wolf et al. | 606/185 |
| 5,746,760 A | 5/1998 | Humphrey, Jr. | 606/171 |

FOREIGN PATENT DOCUMENTS

| | | |
|---|---|---|
| DE | 4440035 | 11/1994 |
| EP | 0555803 A1 | 8/1993 |
| EP | 0555803 B1 | 8/1993 |
| EP | 0621008 | 4/1994 |
| EP | 0761170 | 9/1996 |
| EP | 0806183 | 5/1997 |
| EP | 0807412 | 5/1997 |
| EP | 0841036 | 9/1997 |
| WO | WO94/22508 | 3/1994 |
| WO | WO97/24070 | 12/1996 |
| WO | WO99/07295 | 7/1998 |

*Primary Examiner*—Michael H. Thaler
(74) *Attorney, Agent, or Firm*—St. Onge Steward Johnston & Reens, LLC

(57) ABSTRACT

The invention related to an instrument for cutting biological and notably human tissue, especially during endoscopic surgery, with an outer tube and a hollow, cylindrical cutting tube which is positioned within the outer tube and can be rotated about its longitudinal axis and at whose distal end at least one blade is positioned. The instrument also comprises a manipulator which is mounted at the proximal end of the tubes. The outer tube can be displaced in the axial direction of the cutting tube, which is immovably fixed to the manipulator, against the force of a pressure spring between an initial position in which the outer tube projects beyond the cutting tube on the distal side and a working position in which the blade protrudes from the distal end of the outer tube. The aim of the invention is to improve an instrument of this type in such a way that it is simple and safe to use while giving an operator the greatest possible freedom of movement. To this end the invention provides for the outer tube to be blocked against displacement in the axial direction by means of a blocking element when it is in its initial position. The blocking element contacts the outer tube at the proximal end and can be released via an actuating button positioned on the manipulator. The outer tube thereafter, independently of further activation of the actuator button, can be returned to the working position by the exertion of axial pressure on the outer tube, and the pressure spring automatically returns the outer tube into the blocked initial position after each displacement into the working position.

4 Claims, 2 Drawing Sheets

INSTRUMENT FOR CUTTING BIOLOGICAL AND NOTABLY HUMAN TISSUE

This application is a continuation of pending International Application PCT/00EP/01547 filed Feb. 25, 2000, which designates the United States and claims priority from DE19908721.0 filed Mar. 1, 1999.

FIELD OF THE INVENTION

The invention relates to an instrument for cutting biological and notably human tissue, especially during endoscopic surgery, with an outer tube and a hollow, cylindrical cutting tube which is positioned within the outer tube and can be rotated about its longitudinal axis and at whose distal end at least one blade is positioned. The instrument also comprises a manipulator which is mounted at the proximal end of the tubes. The outer tube can be displaced in the axial direction of the cutting tube, which is immovably fixed to the manipulator, against the force of a pressure spring between an initial position in which the outer tube projects beyond the cutting tube on the distal side and a working position in which the blade protrudes from the distal end of the outer tube.

BACKGROUND OF THE INVENTION

Surgical instruments of this kind, known as morcellators, are used in endoscopic surgical interventions that require the removal of large portions of tissue. These morcellators consist of a power-driven cutting tube, notably an electromechanically driven cutting tube, that can be directly introduced into the body or into a natural or synthetic bodily cavity. In order to remove tissue, a pincer is introduced into the body or bodily cavity to grip the tissue for extraction. When the pincer is then withdrawn and the tissue is pressed against the cutting edge of the rotating morcellator, a cylindrical block of tissue can be cut out through a prescribed pull, and possibly by varying the turning speed and turning direction, and removed through the tube. Even large amounts of tissue can be extracted in this manner within a few minutes.

A medical instrument of this general type is known from EP-A-0 621 008. With this familiar instrument, a button can be activated to move the outer tube from the initial position to the working position in which the blade of the cutting tube protrudes from the outer tube. By pressing the button, a blocking element is displaced, which allows the outer tube directly connected with the button to be withdrawn as far as the manipulator.

Because the button and the outer tube are firmly connected with one another and the button is pre-tensioned by means of a readjusting spring, the operator must hold the button down until the blade of the cutting tube remains in the working position. This circumstance limits the operator's freedom of movement in operating this familiar instrument, since the operator must hold the button permanently pressed down during the cutting process.

In other morcellators, known from EP-B1-0 555 803 and EP-A1-0 806 183, which have a cutting tube positioned within the distal end of the outer tube protruding from the outer tube, there is the danger that the cutting area of the cutting tube is not covered, or cannot be covered, so that injuries can occur through cutting at unintended places. This risk also exists in the morcellator, known from DE-C2-44 40-035, which has a protective tube positioned inside the cutting tube.

Additional medical cutting instruments are familiar from EP-A1-0 841 036 and EP-A1 0 807 412. Both these documents show how to arrange the outer tube and the cutting tube so that they can be moved in relation to one another. The disadvantage of these familiar instruments, however, is that they both require long-term activation of the button in order to move the cutting tube into cutting position. This continuing pressure on the button clearly limits the operator's freedom of movement.

On the basis of this familiar technology, the invention is based on the task to improve a surgical instrument of the type specified at the outset in such a way as to ensure the greatest possible freedom of movement for the operator along with simple and safe maneuverability. The solution of this task through this invention is distinguished in that the outer tube is blocked in the starting position against axial displacement by means of a blocking element which contacts the proximal end of the outer tube and can be unlocked by means of an actuator button positioned on the manipulator in such a way that the outer tube can be displaced thereafter into the working position by exerting axial pressure on the outer tube, independently of an additional activation of the actuator button, and that the pressure spring automatically returns the outer tube to the blocked starting position after each displacement into working position.

This invention's design of the surgical instrument allows the operator the greatest possible freedom of movement because displacing the outer tube from the initial position to the working position requires only a single pressure on the actuator button in order to release the blocking element that is in contact with the proximal end of the outer tube. As soon as the blocking element is released, the operator can also release the actuator button, because displacement of the outer tube over the tissue, secured by means of a pincer instrument through the hollow, cylindrical cutting tube and pulled out to the manipulator, can also proceed in such a way that pressure is exerted on the surgical instrument by means of the manipulator, so that the surrounding outer tube clamping the tissue as a trocar sleeve is displaced into the working position in relation to the cutting tube.

As soon as axial pressure is no longer exerted on the outer tube, this outer tube is automatically returned to the initial position and is once again blocked in this position by the blocking element. No further cutting is possible until the blocking element is again released through pressure on the actuator button.

The blocking effect of the blocking element is reinforced, in addition, by the fact that the blocking element is spring-pressured in blocked position; that is, the blocking element, if it is not released by the actuator button, is automatically returned to the blocked position by means of a pressure spring. In an adaptation of the invention, the blocking of the outer tube by the blocking element is facilitated by the fact that a start incline is provided for the blocking element at the proximal end of the outer tube.

The blocking element is released, in a preferred adaptation of a surgical instrument according to the invention, by means of a pin, which is immovably fixed to the blocking element and which is housed within a curved track positioned in the shaft of the actuator button and can be displaced along the curved track through pressure on the actuator button. By means of this constrained action of the pin spring connected with the blocking element, the blocking element is displaced into unlocked position by activation of the actuator button, that is, through pressure on the housing of the manipulator.

SUMMARY OF THE INVENTION

Finally, it is proposed with this invention that the actuator button itself, against the force of a pressure spring, should be retractable into unblocked position into the housing of the manipulator, so that the actuator button is automatically restored to its initial position after each activation. Additional characteristics and advantages of the invention can be seen in the following description of the related illustrations of a model for an instrument, in accordance with the invention, for cutting biological and notably human tissue. The illustrations are as follows.

BRIEF DESCRIPTION OF THE DRAWINGS

FIG. 2 Detail, schematic longitudinal section of an instrument in accordance with the invention, in the initial position as presented in FIG. 1a.

DETAILED DESCRIPTION OF THE DRAWINGS

Figure 1A:
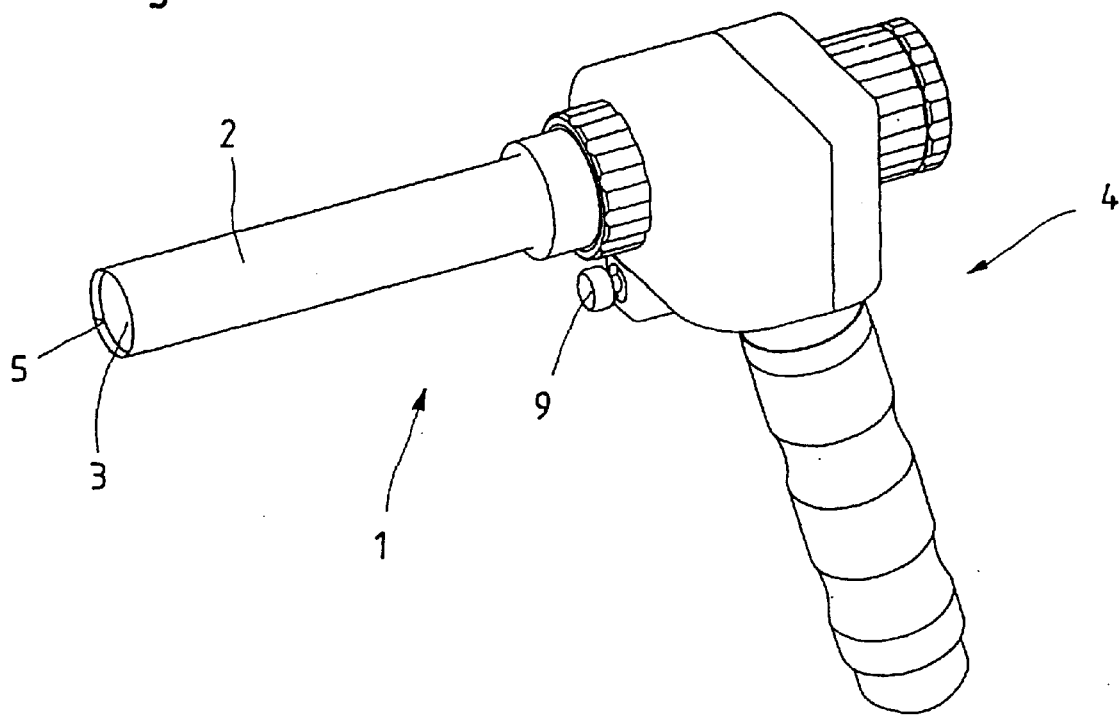
FIG. 1a Perspective view of the invention's instrument in initial position.
Figure 1B:
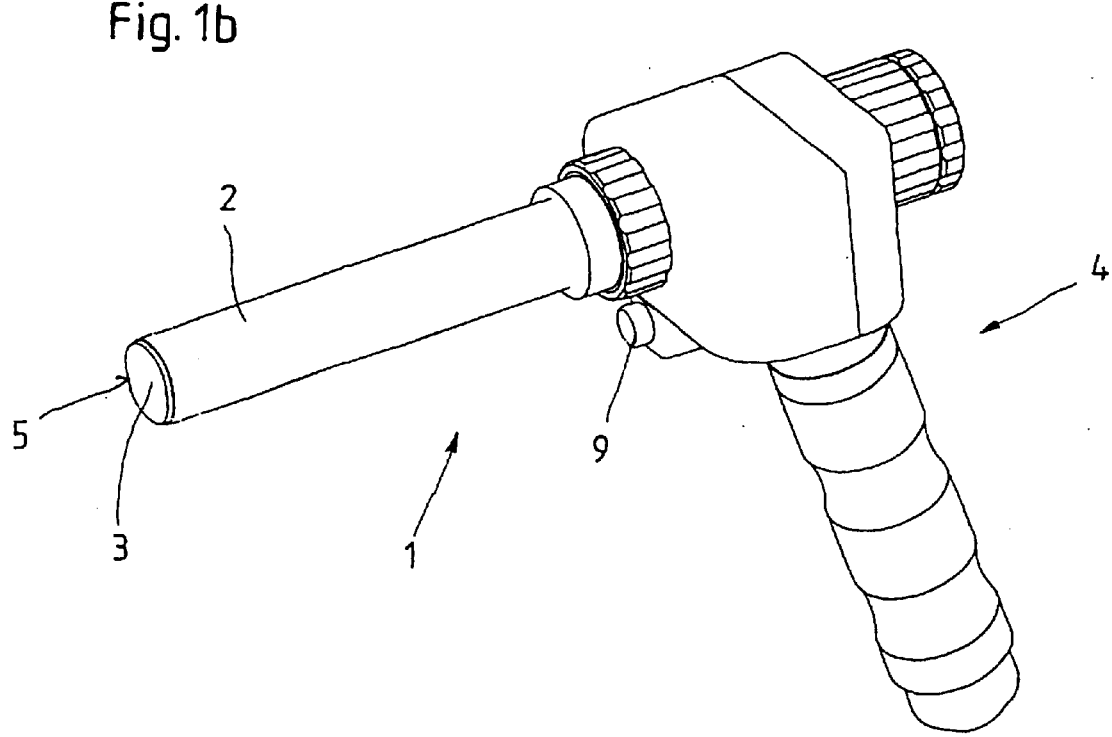
FIG. 1b Perspective view in accordance with FIG. 1a, but with the invention's instrument in working position.

As can be seen from FIGS. 1a and 1b, the surgical instrument designed as the morcellator 1 for cutting biological and notably human tissue consists essentially of an outer tube 2 and a cutting tube 3 which is positioned in the outer tube 2 and has a common manipulator 4 positioned at its proximal end. The distal end of the cutting tube 3 is designed as the blade 5 for cutting biological and notably human tissue.

The illustrations in FIGS. 1a and 1b will differ from one another in that in the initial position of the morcellator 1 in FIG. 1a, the outer tube 2 protrudes beyond the distal end of the cutting tube 3 in such a way that the blade 5 of the cutting tube 3 is entirely covered by the outer tube 2, which coaxially surrounds the cutting tube 3.

Contrary to this, in the working position of the morcellator 1 illustrated in FIG. 1b, the blade 5 of the cutting tube 3 protrudes from the distal end of the outer tube 2, so that the blade 5 can be used for cutting tissue.

Figure 2:
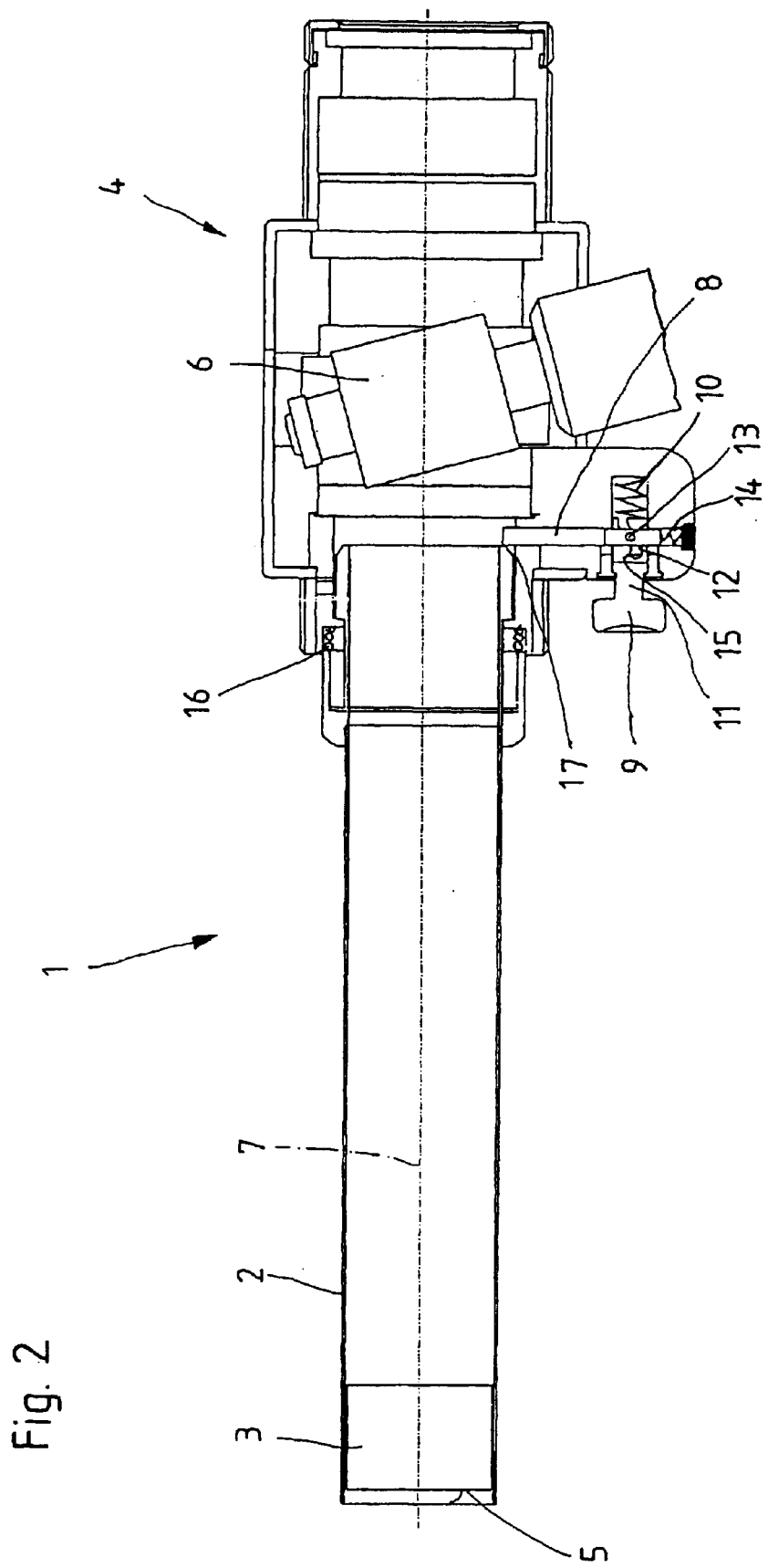

The more precise structure of a morcellator can be seen illustrated in FIG. 2. This longitudinal section through the morcellator 1 shows the latter in the initial position shown in FIG. 1a, in which the cutting tube 3 together with the blade 5 is completely covered by the outer tube 2 on the distal side.

To cut biological and notably human tissue, the cutting tube 3 can be rotated on its longitudinal axis 7 by a power drive 6, for instance a worm drive.

To displace the morcellator 1 from the initial position shown in FIG. 1a to the working position of FIG. 1b, the cutting tube 3 in this illustrated model is immovably fixed to the manipulator 4 in the longitudinal direction, whereas the outer tube 2 is displaceable in relation to the cutting tube 3 axially to longitudinal axis 7. In the initial position, the outer tube 2 is blocked against displacement in the axial direction by a blocking element 8 which contacts the proximal end of the outer tube 2. The blocking element 8 can be released by means of an actuator button 9 positioned on the manipulator 4. To do this, the actuator button 9 is pressed against the force of a pressure spring 10 into the housing of the manipulator 4. A curved track 12 is formed within a shaft 11 of the actuator button 9, and in this curved track 12 a pin 13 is positioned, connected by spring activation with the blocking element 8. As can be seen in FIG. 2, the curved track 12 in the shaft 11 of the actuator button 9 is shaped in such a way that upon pressure on the actuator button 9, the blocking element 8 is pulled downward, by means of the pin 13 positioned in the curved track 12, against the force of a pressure spring 14, out of the position that blocks the outer tube 2. At the end of the curved track 12 there is a stopping point 15 in which the actuator button 9 remains caught in the in-pressed position by means of the pin 13 positioned at the spring-pressured blocking element 8.

In this position, in which the blocking element 8 has released the outer tube 2, the outer tube is now only under the pressure of a pressure spring 16, by which the outer tube 2 is spring-pressured in the initial position.

At this point, if tissue, secured by a pincer (not illustrated) introduced into the cutting tube 3, is drawn in axial direction toward the manipulator 4, the outer tube 2, now axially displaceable relative to the cutting tube 3, is displaced to the manipulator 4 against the return force of the spring 16. The displacement of the outer tube 2 to the manipulator 4 proceeds until, in the working position shown in FIG. 1b, the blade 5 of the cutting tube 3 protrudes out of the distal end of the outer tube 2 and, powered by the power drive 6, cuts out a cylindrical piece of tissue from the tissue secured by the pincer.

When the outer tube 2 is retracted, the blocking element 8 is pressed farther downward by means of a start incline 17 positioned at the proximal end of the outer tube 2, and as a result the pin 13 positioned on the blocking element 8 emerges from the stopping point 15 of the curved track 12 and the actuator button 9 is again pushed outward from the housing of the manipulator 4 by means of the spring 10. At the same time, the spring 14, pressuring the blocking element 8 in the blocked direction, presses the blocking element 8 back upward in the direction of the blocked position.

As soon as pressure ceases against the distal end of the outer tube 2, the outer tube 2 is pushed back into the initial position covering the blade 5 of the cutting tube 3. Simultaneously with this axial displacement of the outer tube 2, the blocking element 8 runs up against the start incline 17 at the proximal end of the outer tube 2 and is returned to the blocked position shown in FIG. 2 at the proximal end of the outer tube 2 by means of the spring 14.

For an additional cutting action, it is necessary first to press in again on the actuator button in order to move the blocking element 8 into the unblocking position releasing the outer tube 2.

With a morcellator 1 of this design, in which the outer tube 2 and the cutting tube 3 can be displaced relative to one another between an initial position completely covering the blade 5 of the cutting tube 3 by means of the outer tube 2 and a working position in which the blade 5 of the cutting tube 3 protrudes from the distal end of the outer tube 2, it is guaranteed that any accidental cutting in unintended places is avoided insofar as possible, because cutting is only possible if the blocking of the initial position is released through the activation of the actuator button 9.

In addition to the possibility, as illustrated and described, of keeping the outer tube 2 displaceable and of keeping the cutting tube 3 firmly in place, it is also possible of course, with an outer tube 2 fixed in the axial direction, to store the cutting tube 3 within the outer tube 2 so it can move between the initial position and the working position.

While the morcellator 1, as described, is intended to be introduced into the body or the bodily cavity directly, that is, without trocar, the described arrangement of the outer tube 2 and the cutting tube 3, which can be displaced in relation to one another, can also be used for morcellators 1 that are designed for insertion by means of an additional trocar.

Operating with the morcellator 1 in accordance with the illustrations of FIGS. 1a, 1b, and 2, proceeds as follows.

For an operation, the morcellator 1 is placed on the body and a trocar pin is injected through the free cross-section of the cutting tube 3. The skin is then penetrated with the trocar pin in order to reach the operating area that has already been prepared in the bodily cavity. Through the injection passage thus provided, the outer tube 2 of the morcellator 1 is introduced into the bodily cavity and the trocar pin is retracted from the morcellator 1.

Using visual monitoring by means of an endoscopic viewing instrument, which has been introduced into the bodily cavity through an additional injection passage, the morcellator 1 is transported to the operating area. To carry out the operation itself, the pincer is then introduced through the free cross-section of the cutting tube 3. The tissue to be removed is secured with the pincer and the pincer is retracted into the cutting tube 3.

To permit removal of the cylindrical piece of tissue by means of the blade 5 of the cutting tube 3, the outer tube 2 is released by pressure on the actuator button 9. By pulling the tissue that is secured by the pincer against the distal end of the outer tube 2, this tube is then displaced in the axial direction to the manipulator 4, until in the working position the blade 5 protrudes beyond the distal end of the outer tube 2. By means of the blade 5 of the power-driven cutting tube 3, a cylindrical piece of tissue is then cut out of the tissue secured with the pincer.

After excision of the tissue piece, as soon as pressure against the distal end of the outer tube 2 ceases, the spring 16 presses the outer tube 2 back to the initial position covering the cutting tube 3.

Additional cutting by means of the cutting tube 3 is only possible if the outer tube 2 is again released and returned to the working position by means of the tissue secured by the pincer.

What is claimed is:

1. Instrument for cutting biological tissue, especially during endoscopic surgery, with an outer tube and a hollow, cylindrical cutting tube which is positioned within the outer tube and can be rotated about its longitudinal axis and at whose distal end at least one blade is positioned, as well as with a manipulator which is mounted at the proximal end of the tubes, whereby the outer tube can be displaced in the axial direction of the cutting tube against the force of a pressure spring between an initial position in which the outer tube projects beyond the cutting tube on the distal side and a working position in which the blade protrudes from the distal end of the outer tube, characterized in that the outer tube is blocked against displacement in the axial direction by means of a blocking element which contacts the proximal end of the outer tube and can be released by means of an actuating button positioned on the manipulator in such a way that the outer tube can then be displaced into the working position independently of additional action of the actuating button by exerting an axial pressure on the outer tube, and that the pressure spring automatically returns the outer tube into the blocked initial position after each displacement into the working position, wherein the blocking element is unlocked via a pin firmly adjoined to the blocking element, which pin is contained in a curved track which is positioned in a shaft of the actuating button and can be moved along this curved track by pressure on the actuating button.

2. Instrument in accordance with claim 1, characterized in that the blocking element is spring-pressured in the direction of the blocked position.

3. Instrument in accordance with claim 1, characterized in that an abutting incline for the blocking element is positioned at the proximal end of the outer tube.

4. Instrument in accordance with claim 1, characterized in that the blocking element is unlocked via a pin firmly adjoined to the blocking element, which pin is contained in a curved track which is positioned in a shaft of the actuating button and can be moved along this curved track by pressure on the actuating button.

* * * * *